United States Patent [19]

Kross

[11] Patent Number: 5,772,986
[45] Date of Patent: Jun. 30, 1998

[54] COMPOSITIONS AND METHODS FOR REDUCING ORAL MALODOR

[76] Inventor: Robert D. Kross, 2506 Florin Ct., Bellmore, N.Y. 11710

[21] Appl. No.: 629,357

[22] Filed: Apr. 8, 1996

[51] Int. Cl.⁶ ........................................ A61K 7/20
[52] U.S. Cl. ............................... 424/53; 424/49
[58] Field of Search ........................... 424/53, 49

[56] References Cited

U.S. PATENT DOCUMENTS

| | | |
|---|---|---|
| 3,123,521 | 3/1964 | Wentworth . |
| 3,585,147 | 6/1971 | Gordon . |
| 4,689,215 | 8/1987 | Ratcliff . |
| 4,696,811 | 9/1987 | Ratcliff . |
| 4,837,009 | 6/1989 | Ratcliff . |
| 5,100,652 | 3/1992 | Kross et al. . |
| 5,185,161 | 2/1993 | Davidson et al. . |
| 5,200,171 | 4/1993 | Ratcliff . |
| 5,281,412 | 1/1994 | Lukacovic et al. . |

*Primary Examiner*—Paul J. Killos
*Attorney, Agent, or Firm*—Henry D. Coleman; R. Neil Sudol

[57] ABSTRACT

The present invention relates to the discovery that the oral malodorant reduction activity of stabilized chlorine dioxide solutions and chlorite solutions may be significantly enhanced through the use of oral-cavity pre-conditioning solutions such as fruit juices, natural fruit-acid solutions and a number of commercial soft drinks which have pH's below about 6. The liquids predispose the oral surfaces and tissues of the mouth and the malodorant molecules associated with these surfaces to be more reactive to and/or affected by the subsequent exposure to the stabilized chlorine dioxide and chlorite oral rinse solutions.

16 Claims, No Drawings

COMPOSITIONS AND METHODS FOR REDUCING ORAL MALODOR

FIELD OF THE INVENTION

The present invention is directed to compositions and their method of use in oral hygiene. More specifically, the present invention is directed to the sequential application of certain chemical compounds as part of a daily regimen in the treatment and reduction of oral malodor.

BACKGROUND OF THE INVENTION

Malodor of the oral cavity, and all related terms such as "bad breath", "halitosis", "foul breath" and "breath malodor," generally refer to the offensive breath odor of one person as detected by another. It has been estimated that 90% of the population exhibits oral malodor upon arising (e.g. "morning mouth") which persists throughout the day in about 20% of American adults. Such oral malodor is not directly detectable by the sufferer, who only becomes aware by the revealing actions of others. In addition to immediate embarrassment, oral malodor can cause a significant interference with the enjoyment of everyday life, affecting career advancement as well as family and societal relationships.

Contrary to general belief, at least 90% of the malodors in healthy persons are produced by local oral conditions. Normal lung air and stomach aroma do not significantly contribute to oral malodor, although various localized respiratory infections, organ system diseases, medications and metabolic disorders can cause malodorous breath. The causes of "morning mouth" and the bad breath which lasts through the day are basically the same, i.e. the putrefactive activity of certain oral bacteria on the sulfur-containing amino acids in oral organic matter such as cellular debris, food particles, and salivary proteins. This degradation by anaerobic bacteria results in the formation of volatile, odiferous sulfur compounds, consisting primarily of hydrogen sulfide, methyl mercaptan, and to a lesser extent other thiols and disulfides, which are then exhaled in the breath. The products are called by the group term "volatile sulfur compounds" (VSC) and may be detectable in air at parts per billion levels. In sleep, a depleted local oxygen availability, lower salivary flow, and the reduced action of the tongue and cheeks, enhance the action of these bacteria. These effects, however, are overcome by most healthy people in the waking state.

Mouthwash users seem to experience little lasting effect from such use, since these formulations generally act as temporary masking agents that briefly supplant the malodor with a more pleasant one. Such rinses may also wash away some of the organic debris upon which the bacteria thrive, but they cannot eliminate the root cause of the malodor in those who are prone to the condition.

Prior art disclosures have included treatments for halitosis whereby the oral cavity is rinsed with an aqueous solution of stabilized chlorine dioxide. Examples include U.S. Pat. Nos. 5,200,171; 4,837,009; and 4,689,215, all issued to Perry A. Ratcliff. These patents are all directed to compounds or methods for treating malodors of the mouth which include "stabilized chlorine dioxide". The expression "stabilized chlorine dioxide" (SCD) as used by Ratcliff in his patents, rather than being directed to chlorine dioxide which has been stabilized in some fashion, actually refers to an aqueous solution whose active agent comprises sodium chlorite. Confusion arises because SCD is actually sodium chlorite in solution, which may be formed by converting chlorine dioxide in solution to chlorite, using a compound such as sodium persulfate. The reaction results in the reduction of the chlorine dioxide to sodium chlorite, which remains in solution for extended periods of time. Another way to produce SCD, is to add bulk sodium chlorite to water in combination with a buffer or a peroxy compound, which will stabilize the chlorite and prevent it from slowly converting to chlorine dioxide. In sum, a solution of SCD as described in the art need not contain any significant or even measurable quantities of chlorine dioxide, and in most instances, the chlorine dioxide in such solutions exists as chlorite at or near a neutral pH and above.

The tendency of sodium chlorite to slowly transform to chlorine dioxide as well as other inactive chlorine species, is the basis for the claimed activity of SCD solutions in correcting oral malodor. In the Ratcliff patents, for example, the SCD is reported to be present in concentrations which produce between 0.05% and 0.1% chlorine dioxide, which corresponds to actual sodium chlorite levels of 0.067% and 0.134% in the solution.

Another use of SCD in the oral cavity is described by Ratcliff, in U.S. Pat. No. 4,696,811 for the reduction of dental plaque and the inhibition of the growth of the microorganism primarily responsible for plaque formation. An additional chlorite-containing oral composition is found in U.S. Pat. No. 5,281,412. The composition taught comprises chlorite and citrate ion compositions, at a pH from about 5.9 to about 6.5, where the chlorite acts as a chlorous acid liberating material, and the composition is claimed to provide antiplaque and antigingivitis benefits. The reference is silent as to the control of oral malodor by the chlorite/citrate formulations.

The use of chlorous acid formulations for oral hygiene, based on acidified chlorite solutions, is taught by U.S. Pat. No. 5,100,652, to Kross et al., and by U.S. Pat. No. 5,185,161 to Davidson and Kross, for more general disinfection of substrates. The oral hygiene patent is directed to processes and antimicrobial compositions in which an organic acid in the concentration range of about 0.01% to about 3% is combined with an aqueous metal chlorite at a concentration of about 0.0001% to about 0.4%. The compositions and methods are not directed to the control of oral malodor. The Davidson patent combines an organic acid, in the 0.01% to 6% concentration range, with a metal chlorite in the 0.0001% to 0.45% range, to form chlorous acid compositions for disinfecting substrates. Example 1 of that patent provides a mouthwash formulation with improved bacterial, fungicidal and taste properties that may aid in plaque reduction. The disclosure is directed to the antimicrobial control of oral disease conditions, rather than the chemical control of oral malodor.

One recent, commercially-available composition is reported to offer good control of oral mouth odor. Its active ingredient is gaseous chlorine dioxide, in contrast to stabilized chlorine dioxide which is the basis for other compositions used to treat mouth malodor. SCD is believed to be relatively ineffective in controlling oral malodors compared to the presence of dissolved gaseous chlorine dioxide present in this composition. This is attributed to the fact that aqueous chlorite solutions are relatively stable at near-normal pH's, and will gradually transform to free (active) chlorine dioxide in an oral environment at too slow a rate to produce sufficient levels of chlorine dioxide to effectively destroy substantially all the odor causing agents.

Although a dissolved, gaseous chlorine dioxide treatment is reportedly effective in combatting oral malodor, it is cumbersome and expensive to practice. Prior to initiation of this treatment, a visit is required to a specific practitioner's office, where an oral examination, a breath evaluation and mucosal debridement are performed. The practitioner then supplies gaseous chlorine dioxide solution to the patient for home use. Because aqueous chlorine dioxide will gradually degrade and/or evaporate, additional potent chlorine dioxide compositions must be furnished periodically, with freshly-prepared product re-supplied through a delivery service. People who strive to control their oral malodor, and who must use this composition continually to keep their condition in check, find this approach costly and inconvenient.

It is apparent that no readily stable composition and patient friendly process is available for patients having oral malodor problems. In addition, present practice lacks convenient and effective methods and compositions to treat and control malodor, such that a full treatment can be carried out economically in the home with a storage stable composition. There is a clear need in the art for an effective and economical means of treating and controlling oral malodor and eliminating the negative social stigma associated with this condition. The present invention is the direct result of a search for methods to improve the effectiveness of the previously-taught stabilized chlorine dioxide formulations, and their basic component, sodium chlorite.

OBJECTS OF THE INVENTION

It is, therefore, an object of the present invention to provide a composition and a process for providing a treatment for halitosis or mouth malodor.

It is a further object of the present invention to enhance the effectiveness of current stabilized chlorine dioxide and chlorite-containing malodor formulations by creating a chemical environment in which the composition and process function more effectively.

It is still an additional object of the present invention to enhance the effectiveness of current stabilized chlorine dioxide and chlorite-containing malodor formulations by creating a physical environment in which the composition and process function more effectively.

It is yet a further object of the present invention to substantially alleviate the disadvantages inherent in prior art procedure.

These and/or other objects of the present invention may be readily gleaned from a detailed review of the description of the invention which follows.

SUMMARY OF THE INVENTION

The present invention relates to the discovery that the activity of stabilized chlorine dioxide and chlorite in solution may be significantly enhanced through the use of oral-cavity pre-conditioners. These pre-conditioners comprise fruit juices, natural fruit-acid solutions, a number of commercial soft drinks or mixtures thereof, all of which have solution pH's below about 6. These liquids predispose the oral surfaces and tissues to be more reactive to and/or affected by the subsequent exposure to the stabilized chlorine dioxide and chlorite oral rinse solutions. The fruit juices useful for this application include for example, apple, beet, cranberry, orange, grape, pineapple, grapefruit, lemon, and prune juices, and combinations thereof (e.g. fruit punch). The natural fruit acids useful for this application include adipic, citric, fumaric, gluconic, lactic, succinic, malic, tartaric, and their combinations. Appropriate commercial soft drinks which are suitable for use in this invention include carbonated soft drinks, for example, birch beer, cream soda, cherry soda, colas, ginger ale, grape soda, grapefruit soda, lemon soda, lemon lime soda, orange soda, peach soda, quinine water, raspberry soda, root beer, sarsaparilla, and strawberry soda.

In another aspect, the present invention provides a method for enhancing the activity of stabilized chlorine dioxide and chlorite solutions through the use of a physical debridement of superficial tongue matter, applied prior to introduction of the pre-conditioning liquid. The superficial matter includes bacterial build-up, sloughed cells and residual food particles. The removal of tongue matter according to the present invention allows for a more effective wetting of the crevices and fissures of the tongue by the pre-conditioning liquid, so that the subsequently applied stabilized chlorine dioxide or chlorite solution will be more effectively used in these areas. Scraping away the coating on the dorsa-posterior portion of the subject's tongue, from its center to the rear wart-like bumps at the neck, using an appropriately shaped brush or scraper, facilitates the penetration of the liquid into the underlying crevices and grooves. The acidity of the liquid creates a micro-environment where the subsequently-applied stabilized chlorine dioxide or chlorite treatment can function more effectively. Nevertheless, the concentration of free acid in the subsequent oral rinse treatment, as a residual from the pre-conditioning liquid in the oral cavity, is generally below 0.001% for the organic fruit acids, and below about 0.0001% for inorganic acids such as phosphoric, that are often found in some commercial soft drinks.

According to another aspect of the invention, a kit is provided that will allow an individual to carry out a complete home treatment for the remediation or elimination of oral malodor, without the need for an initial visit to a clinical facility where professional care must first be administered. The kit comprises a) either a solution of a fruit juice or fruit acid concentrate, or instructions how to utilize a commercially-available juice or soft drink in this invention, b) a solution of stabilized chlorine dioxide or chlorite, or a concentrate thereof, c) large empty containers to be used for aqueous dilution of concentrates, when supplied, d) a scraper or brush for debridement of oral surfaces and e) instructions on the proper use of the kit.

DETAILED DESCRIPTION OF THE PRESENT INVENTION

The term "subject" is used throughout the specification to describe an animal, including a human to whom treatment with the compositions and methods according to the present invention is provided. The invention primarily contemplates the treatment of humans in office and home settings, but veterinary applications are also within the scope of the present invention.

The term "effective concentration" or "effective amount" is used to describe an amount or concentration of an agent such as the pre-conditioning liquid, stabilized chlorine dioxide or chlorite solution or fluoride salt or other additives included in the present invention to produce an intended result. For example, in the case of a pre-conditioning liquid, the amount of such liquid used in the present invention is that amount which is effective for substantially enhancing the ability of the stabilized chlorine dioxide solution or the chlorite solution to reduce malodor in the mouth of the subject. In general, an effective amount of a pre-conditioning liquid provides sufficient acidity in the mouth environment after expunging the liquid from the mouth to provide no greater than about 0.001% by weight acid in combination with the stabilized chlorine dioxide or chlorite solution. An effective concentration of stabilized chlorine dioxide or chlorite is that amount which substantially reduces malodor in a treated subject in combination with the pre-condition liquid.

The present invention provides an oral rinse liquid which significantly enhances the effectiveness of a subsequent oral rinse with aqueous stabilized chlorine dioxide or sodium chlorite oral treatment, for the treatment of oral malodor, or bad breath. Stabilized chlorine dioxide solutions are known in the art to contain predominantly sodium chlorite, often with added stabilizers such as buffers, but little free chlorine dioxide. The art recognizes that much of the effectiveness of these solutions is achieved when the stabilized chlorine dioxide contacts the acids produced by growing bacteria, which triggers the formation of chlorine dioxide and destroys the odor causing chemical agents. It is also known that the same conversion to chlorine dioxide occurs when a stabilizer-free chlorite solution contacts a similar triggering environment.

In pursuing means for substantially enhancing the effectiveness of currently-marketed stabilized chlorine dioxide solutions, which at best offer little remediation of oral malodor, it has been discovered that by first drinking, or even rinsing the mouth with a number of common liquid materials, such as fruit juices and commercial soft drinks, a similar, but enhanced environment will be created such that a subsequent rinse with a stabilized chlorine dioxide or a chlorite solution will remarkably reduce detectable oral malodor. It has also been determined that the same enhanced reduction of bad breath can be achieved by first drinking or rinsing the mouth with a synthetic fruit drink, composed of fruit acids and flavorants, or fruit acids alone, or synthetic soft drinks, or even the acidic substances such as phosphates used in the formulation of such drinks.

The fruit juices which successfully enhance the malodor destroying ability of stabilized chlorine dioxide or chlorite solutions include apple, beet, cranberry, orange, grape, pineapple, grapefruit, lemon, and prune juices, and combinations thereof. Commercial soft drinks which have been found to function in a similar capacity include birch beer, cream soda, cherry soda, colas, ginger ale, grape soda, quinine water, raspberry soda, root beer, sarsaparilla, and strawberry soda. Specialty drinks such as fruit punch and Gatorade also are suitable as pre-treatment drinks or mouth rinses. It is preferred that the drink have a pH of less than about 6.0, more preferably less than about 5.0, even more preferably, about 4.5 or less. The natural fruit acids useful for this application include adipic, citric, fumaric, gluconic, lactic, succinic, malic, tartaric, and their combinations. Other acids such as phosphoric (used in phosphated drinks) and even acetic (in vinegars) also create an environment similar to that created by growing, acid-producing bacteria, such as lactic acid Streptococci. In addition products such as yogurts, which are created by such lactic-producing bacteria, as well as sour milk and sour cream will enhance the odor-destruction achieved through subsequent oral rinsing with a stabilized chlorine dioxide or a chlorite solution.

It has also been discovered that successful pre-conditioning of oral surfaces, particularly the tongue, requires that extraneous oral debris be first reduced or eliminated. This oral debris, which is often termed plaque, primarily resides on the upper tongue surface, from its mid-point back. It generally consists of bacterial and human cellular debris and food residues, and has a semi-coherent sponge-like consistency. When the pre-conditioning liquid becomes entrapped in this matter, followed thereafter by the stabilized chlorine dioxide or chlorite solution, the resulting oxidizing power of the treatment is subsequently dissipated by competitive reaction with the plaque components rather than the sulfur-containing malodorant molecules. Therefore this entrapping material must be initially removed, prior to contact with the pre-conditioning liquid, and this can be accomplished with any of the many tongue scrapers commercially available, or even with an ordinary tooth brush.

For the use of this invention in the home, it is advantageous to employ a standardized pre-conditioning solution, so that the subject will be able to establish a uniform daily practice for treating his or her mouth odor condition. The random daily use of one or another fruit drink or soda, which would result in variable pre-conditioning of mouth surfaces and inconsistent results, can be readily overcome through daily use of a standard liquid solution containing a constant level of a fruit acid. For ease, convenience and economy, this fruit acid preferably can be supplied in a concentrated form suitable for distribution through private or postal delivery services.

The amount of fruit acid or other pre-conditioning acidifier that may be used in the compositions of this invention is dependent upon the nature and strength of the acidifier, its palatability and whether the intended preparation will be a concentrate or a ready-to-use solution. The following ranges of use are based on the preparation of a ready-to-use solutions, and these levels would be multiplied by the degree of concentration if the intended solution is a concentrate. For the organic fruit acids, individually or in combination, an aqueous solution consists essentially of from about 0.05% to about 5% by weight acid. For inorganic strong acids such as phosphoric acid, individually or in combination, an aqueous solution consists essential of about 0.01% to about 2% by weight acid. For a weak inorganic acid such as carbonic acid, the level of use would depend on the pressure and solubilization capability.

The fruit acid, in concentrated or direct-use form, can optionally contain flavorants, colorants and sweeteners in order to increase the palatability and appearance of the products. Such additives are well known by those skilled in the art, and include the following: Flavorants- natural and synthetic; cherry, apple, citrus, pineapple, grape, strawberry and cranberry; used individually or in combination. Colorants- FD&C Yellow No. 5 and 6, Red No. 4 and 40, Green No. 3, Blue No. 1, and natural food color extracts; used individually or in combination. Sweeteners- Sucrose, fructose, dextrose, fructose-enhanced corn syrups, as well as such artificial sweeteners as sodium saccharine and aspartame; used individually or in combination. When concentrated fruit-acid solutions are being prepared, the use of natural carbohydrate sweeteners are generally precluded. The level of use of each of these additive types can be well determined by those skilled in the art of formulating related juice compositions, and need not be further elaborated upon.

The stabilized chlorine dioxide or chlorite solutions, whose action in reducing oral malodor are enhanced by the above-described oral surface pre-conditioning, may be any of several that are commercially available for such purposes, such as Oxyfresh, or Purogene sold by Oxyfresh U.S.A., or they can be prepared from concentrates, such as the 5% stabilized chlorine dioxide concentrate Anthium Dioxcide, sold by International Dioxcide, or by simple dilution of sodium chlorite solid or solution concentrates, such as available from Vulcan Chemical. The concentration of stabilized chlorine dioxide reported by Ratcliff, in U.S. Pat. No. 4,689,215, as effective in reducing the production and origin or oral malodor, is in the range of 0.005% to 0.2%. When using the equivalent solution concentrations of sodium chlorite, which is the major component of stabilized chlorine dioxide products, the aqueous concentrations of sodium chlorite are in the range of about 0.0067% to 0.27%. When using sodium chlorite solutions, which tend to decompose at pH's near 7, it is important to adjust their pH values to 9.0 or above, in order to prevent such degradation. The adjustment should be made with a simple alkali, such as sodium hydroxide, rather than a buffer or an alkaline material which will form a buffer. Thus, certain preferred embodiments according to the present invention contain an absence of a buffer or a material which will form a buffer. The use of buffers will interfere with, and suppress the desired interaction of the chlorite and the pre-conditioned oral surfaces. When the stabilized chlorine dioxide or sodium chlorite solutions are supplied as concentrates to the consumer, the alkalinity of the concentrations should be adjusted such that the intended dilution will have a pH of 9.0 or above, preferably in the absence of a buffer or a material which forms a buffer.

A convenient means of dispensing both the pre-conditioning and treatment solutions described above, involves the use of liquid volumes that can be contained in the inverted bottle caps of two containers. The following is an exemplary oral deodorizing regimen in accordance with this invention. It incorporates the optional use of a tongue scraper, to facilitate pre-conditioning the tongue surface, and a toothbrush, to promote contact of the stabilized chlorine dioxide or chlorite solution with the subject's oral surfaces. It is noted that the steps may be used in virtually any order to enhance the activity of chlorite solutions in substantially reducing mouth odor.

Step 1—Extend the tongue fully, and apply a plastic tongue scraper to the full top surface of the tongue, scraping back as far as possible without promoting gagging. Remove any white coating that is evident. This process can take up to 30 seconds or more to accomplish, depending on the degree of tongue coating.

Step 2—Vigorously swish 1 capful of the pre-conditioning liquid in the mouth for 30 seconds, and spit out the liquid.

Step 3—Take 1 capful of the stabilized chlorine dioxide or chlorite solution into the mouth and then insert a toothbrush, gently working the solution into the gum line on both sides of the teeth. Seal the lips around the toothbrush to prevent the loss of the liquid rinse. Then brush the gums, cheeks, palate and inner lip surfaces for 30 seconds, before spitting out the liquid. Do not take any other liquids in the mouth for at least 10 minutes thereafter.

This above-described procedure can be varied, in several ways, depending on individual user preference, e.g. by eliminating the use of the scraper and/or the toothbrush, by using the scraper after the pre-conditioning step but before the treatment, and by holding the solutions in the mouth for longer or shorter periods.

Although the present invention relies on the use of a pre-conditioning fluid comprised of a fruit juice, a fruit acid solution, or a commercially-available soft drink, all of which are acidic in nature, analysis of the stabilized chlorine dioxide or chlorite rinse solution in the mouth, after use of the pre-conditioner, has revealed no residual acidity in the rinse solution. Specifically, no intact and unionized organic fruit acid could be found in expectorated stabilized chlorine dioxide or chlorite treatment solutions, at a detection limit of about 0.001%. A corresponding maximum level of 0.0001% of inorganic acid, such as phosphoric, has also been established. It is a surprising result that the use of the pre-conditioning solution would substantially enhance the activity of the stabilized chlorine dioxide or chlorite solution to reduce mouth odor without evidencing concentrations of acid which traditionally have been associated with the production of chlorine dioxide.

In the practice of this invention, which utilizes acidic pre-conditioning fluids as a necessary first step to enhance the effectiveness of oxychlorine oral deodorants, a fluoride salt may be optionally included in the pre-conditioning liquid to counter any concern about tooth dimineralization by the acidic pretreatment. When it is desired to include a fluoride salt, its level of use is in the range of about 0.005% to about 0.05% as the fluoride ion, with a preferred range of 0.01% to 0.02% in that form. Preferred fluoride salts include for example, sodium fluoride, sodium monofluorophosphate as well as other fluoride salts.

Having generally described the invention, reference is now made to the following examples intended to illustrate preferred embodiments and comparisons but which are not to be construed as limiting to the scope of this invention as more broadly set forth above and in the appended claims.

In the following examples, unless otherwise noted, all parts and percentages in the examples, as well as the instant disclosure and claims, are understood to be by weight.

EXAMPLE 1

This Example illustrates the use of the present invention for the amelioration of oral malodor. A subject rinses his mouth for 30 seconds with 15 ml (½-ounce) of fresh orange juice, and then swallows it. Immediately thereafter he takes into his mouth 15 ml (½-ounce) of a 0.1% stabilized chlorine dioxide solution, and rinses the oral cavity for 30 seconds prior to spitting out the solution.

EXAMPLE 2

The method of Example 1 is used, except that prior to rinsing with the juice, a plastic scraper is applied to the upper surface of the tongue to scrape it free of removable plaque material consisting of loose cells, food debris and other organic detritus which could otherwise impede effective contact of the pre-conditioning fluid and the tongue surface.

EXAMPLE 3

The method of Example 1 is employed, except that prior to use of the stabilized chlorine dioxide solution a plastic scraper is applied to the upper surface of the tongue to scrape it free of removable plaque material consisting of loose cells, food debris and other organic detritus which would otherwise impede effective contact of the stabilized chlorine dioxide fluid with the pre-conditioned tongue surface.

EXAMPLE 4

The method of Example 3 is employed, except that after taking the stabilized chlorine dioxide solution into the mouth, a toothbrush is inserted through sealed lips, and the solution is gently worked into the gum line, cheeks, palate, inner lips and tongue surfaces. After 30 seconds, the solution is spit out, and replaced with an additional 15 ml of stabilized chlorine dioxide solution which is rinsed and retained for 30 seconds.

EXAMPLES 5–8

The methods according to Examples 1–4 are employed, except that a solution comprised 0.355% malic acid, and 0.05% sodium benzoate is used in place of the orange juice for pre-conditioning the oral cavity surfaces.

EXAMPLES 9–12

The methods according to Examples 1–4 are employed, except that a solution comprised of 0.134% sodium chlorite and 0.022% sodium fluoride, adjusted to pH 9.5 with sodium hydroxide, is used in place of the stabilized chlorine dioxide solution to reduce oral malodorants.

EXAMPLES 13–14

The methods according to Examples 5–8 are employed, except that a solution comprised of 0.134% sodium chlorite and 0.022% sodium fluoride, adjusted to pH 9.5 with sodium hydroxide, is used in place of the stabilized chlorine dioxide solution to reduce oral malodorants.

EXAMPLES 15–18

The methods according to Examples 1–4 are employed, except that a commercial phosphated cola drink is used in place of the orange juice for pre-conditioning of the oral cavity surfaces.

EXAMPLES 19–22

The methods according to Examples 5–8 are employed, except that a solution comprised of 0.055% phosphoric acid, and 0.05% sodium benzoate is used in place of the orange juice for pre-conditioning of the oral cavity surfaces.

It is to be understood that the examples and embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

What is claimed is:

1. A method for treating oral malodor in a subject comprising exposing oral surfaces and tissues of the mouth to an effective amount of a pre-conditioning liquid in a first step to produce an acidic environment on said oral surfaces and tissues of the mouth for reaction with a subsequent chlorite solution and subsequently exposing said exposed surfaces and tissues to an aqueous solution containing a concentration of chlorite effective to substantially reduce the oral malodor.

2. The method according to claim 1 wherein said pre-conditioning liquid is selected from the group consisting of fruit juices, natural fruit-acid solutions and carbonated soft drinks.

3. The method according to claim 2 wherein said fruit juice is selected from the group consisting of apple, beet, cranberry, orange, grape, pineapple, grapefruit, lemon and fruit punch.

4. The method according to claim 2 wherein said fruit-acid is selected from the group consisting of adipic, citric, fumaric, gluconic, lactic, succinic, malic, tartaric and mixtures thereof.

5. The method according claim 2 wherein said pre-conditioning liquid is a carbonated soft drink.

6. The method according to claim 1 further comprising the step of physically debriding superficial tongue matter from the subject's tongue.

7. The method according to claim 1 wherein said solution comprises a fluoride salt.

8. A method for treating oral malodor in a subject comprising exposing oral surfaces and tissues of the mouth of said subject to a pre-conditioning liquid, expunging said pre-conditioning liquid from said subject's mouth to produce an acidic environment in the mouth and then exposing said surfaces and tissues in said mouth to a solution containing a concentration of chlorite effective to substantially reduce the oral malodor, said pre-conditioning liquid producing a concentration of pre-conditioning acid in combination with said chlorite solution of below about 0.001% by weight.

9. The method according to claim 8 wherein said pre-conditioning liquid is selected from the group consisting of fruit juices, natural fruit-acid solutions and carbonated soft drinks.

10. The method according to claim 9 herein said fruit juice is selected from the group consisting of apple, beet, cranberry, orange, grape, pineapple, grapefruit, lemon and fruit punch.

11. The method according to claim 8 wherein said fruit-acid is selected from the group consisting of adipic, citric, fumaric, gluconic, lactid, succinic, malic, tartaric and mixtures thereof.

12. The method according claim 8 wherein said pre-conditioning liquid is a carbonated soft drink.

13. The method according to claim 8 further comprising the step of physically debriding superficial tongue matter from the subject's tongue.

14. The method according to claim 8 wherein said solution comprises a fluoride salt.

15. The method according to claim 8 wherein said fruit-acid solution comprises at least one organic fruit acid in an amount ranging from about 0.05% to about 5% by weight.

16. The method according to claim 8 wherein said stabilized chlorine dioxide or chlorite solutions has a pH of at least about 9.0 and contains an absence of a buffer or a material which forms a buffer.

* * * * *